(12) United States Patent
Bornzin et al.

(10) Patent No.: US 6,636,766 B2
(45) Date of Patent: Oct. 21, 2003

(54) SYSTEM AND METHOD FOR PREVENTING SUDDEN HEART RATE DROP USING IMPLANTABLE CARDIAC PACING DEVICE

(75) Inventors: Gene A. Bornzin, Simi Valley, CA (US); Junyu Mai, Valencia, CA (US); Euljoon Park, Stevenson Ranch, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 207 days.

(21) Appl. No.: 09/849,723

(22) Filed: May 3, 2001

(65) Prior Publication Data

US 2002/0004671 A1 Jan. 10, 2002

Related U.S. Application Data

(60) Provisional application No. 60/204,295, filed on May 15, 2000.

(51) Int. Cl.$^7$ ............................................... A61N 1/365
(52) U.S. Cl. .......................................... 607/19; 607/17
(58) Field of Search ............................... 607/9, 11, 14, 607/15, 17–26

(56) References Cited

U.S. PATENT DOCUMENTS

| | | | |
|---|---|---|---|
| 5,292,341 A | | 3/1994 | Snell ............................ 607/30 |
| 5,466,254 A | | 11/1995 | Helland ....................... 607/123 |
| 5,549,649 A | | 8/1996 | Florio et al. .................. 607/15 |
| 5,725,561 A | * | 3/1998 | Stroebel et al. ................ 607/9 |
| 5,792,193 A | | 8/1998 | Stoop ............................ 607/14 |
| 2002/0091415 A1 | * | 7/2002 | Lovett et al. ................. 607/14 |

OTHER PUBLICATIONS

Barold, S. Serge, et al., "Recent Advances in Cardiac Pacing" Goals for the 21$^{st}$ Century, Futura, 1997, pp. 92–95.
Benditt, David G. MD, et al., "Cardiac Pacing for Prevention of Recurrent Vasovagal Syncope", Ann Intern Med., 1995, 122 pp. 204–209.
Lee, John K., et al., "Acute Testing of the Rate–Smoothed Pacing Algorithm for Ventricular Rate Stabilization", PACE, vol. 22, Apr. 1999, Part I, pp. 554–561.

* cited by examiner

Primary Examiner—George R. Evanisko

(57) ABSTRACT

A rate smoothing technique is applied by the pacing device to sensed and paced heart signals so as to prevent a sharp drop in heart rate, particularly for use within patients prone to vasovagal syncope. The rate smoothing technique is applied by the pacing device during the calculation of an escape interval employed by the device in determining whether to pace the heart. The rate smoothing technique has the effect of adjusting the escape interval to ensure the heart is paced for a period of time subsequent to a sharp drop in the natural heart rate of the patient permitting the heart rate to decrease gradually rather than suddenly. The rate smoothing technique however does not interfere with a sharp increase in heart rate as may be required during sudden physical exertion. System and method examples are described herein.

9 Claims, 4 Drawing Sheets

SYSTEM AND METHOD FOR PREVENTING SUDDEN HEART RATE DROP USING IMPLANTABLE CARDIAC PACING DEVICE

This appln claims benefit of Prov. No. 60/204,295 filed May 15, 2000.

FIELD OF THE INVENTION

The invention generally relates to cardiac pacing techniques and in particular to techniques for preventing a sudden drop in heart rate as may be caused by vasovagal syncope or other disorders.

BACKGROUND OF THE INVENTION

Syncope is a sudden loss of strength or consciousness caused by reduced cerebral circulation, itself typically the result of vasodilation. Vasovagal syncope is a type of syncope referred to as a neurocardiogenic syncope wherein the syncope is triggered by an interaction between the heart and nerve tissue connected to the heart. Neurocardiogenic syncope may also be referred to as neuromediated syncope, neurally mediated syncope, cardioneurogenic syncope, vasodepressor syncope, malignant vasovagal syndrome, neurally mediated hypotension/bradycardia and cardiovascular neurogenic syncope. For vasovagal syncope, the interaction occurs between the heart and the vagus nerve.

Evidence suggests that vasovagal syncope is initially triggered by a sudden reduction in peripheral vascular resistance, perhaps resulting from stress, pooling of blood in the extremities, or other factors. As a result of the reduction in peripheral vascular resistance, the pressure of blood entering the heart drops and the amount of blood filling the ventricles prior to ventricular contractions therefore also drops. With less blood in the ventricles, the ventricles thereby contract much more quickly and vigorously than would otherwise occur in an effort to maintain a constant stroke volume. The more vigorous ventricular contractions have the effect of stimulating ventricular mechanoreceptors, also known as C fibers, that normally only respond to ventricular expansion or stretching, rather than contraction. The activation of the ventricular mechanoreceptors results in a surge in neural traffic to the brainstem, particularly to the nucleus tractus solitaries, via the vasovagal nerve.

For most people, the neurological system properly interprets the increase of activity of the mechanoreceptors as being in response to a drop in peripheral vascular resistance and compensates by increasing the heart rate and constricting the blood vessels. However, in certain patients, as a result of a neurological condition within the vagus nerve or for some other reason, the surge in neural traffic is falsely perceived by the neurological system as being representative of hypertension. In response thereto, the brainstem triggers an increase in peripheral vasodilation and a reduction in heart rate. The vasodilation and the drop in heart rate, in turn, cause a still further reduction in blood pressure, i.e. hypotension. In other words, the actions taken by the brainstem exacerbate the problem. If the degree of hypotension is sufficiently severe, cerebral hypoperfusion occurs wherein brain cells do not receive enough oxygen and, consequently, the victim loses consciousness. Accordingly, within these patients, any sudden drop in peripheral vascular resistance can trigger vasovagal syncope and the patients are then to suffer from recurrent vasovagal syncope. Further information regarding vasovagal syncope may be found in S. Serge Harold and Jacques Mugica, *Recent Advances in Cardiac Pacing*, Futura Publishing Company, 92–95, 1997.

As can be appreciated, loss of consciousness can be particularly dangerous for the patient if occurring while the patient is driving a motor vehicle, climbing a flight of stairs or engaged in any other activity wherein the loss of consciousness could result in injury or death. Accordingly, it is highly desirable to provide techniques for preventing vasovagal syncope or other forms of neurocardiological syncope. One possible technique for preventing vasovagal syncope is to employ a pacemaker, or other implantable cardiac pacing device, to pace the heart to prevent the reduction in blood pressure associated with vasovagal syncope from occurring. Indeed, the American College of Cardiology-American Heart Association suggested in 1991 that vasovagal syncope in patients should be used as a Class 2 indication for pacing therapy. However, conventional cardiac pacemakers have had only limited success in preventing recurrent vasovagal syncope. (See David G. Benditt et al., *Cardiac Pacing for Prevention of Recurrent Vasovagal Syncope*, Ann Intern Med. 1995; 122; 204–209.)

With many conventional techniques for preventing vasovagal syncope, the cardiac pacemaker analyzes a sequence of intrinsic heart beats (i.e. natural or non-stimulated heart beats) to determine whether the sequence of heart beats indicates an episode of vasovagal syncope and, if so, the pacemaker then begins pacing the heart. In one example, if the intrinsic heart rate falls below a lower threshold, the pacemaker then analyzes the immediately preceding heartbeats to determine whether a sharp drop in heart rate has occurred. If so, the pacemaker then continues to monitor intrinsic heart beats to determine whether the heart rate remains at a stable rate below the threshold rate. If the rate remains stable for a predetermined number of heartbeats, the pacemaker then concludes that an episode of vasovagal syncope may be occurring and begins pacing at an elevated heart rate. Unfortunately, by the time the pacemaker has had the opportunity to analyze a sufficient number of heart beats to determine whether an episode of vasovagal syncope is occurring, the blood pressure of the patient has likely dropped to the point where an elevated heart rate will not remedy the vasovagal syncope and the patient will become unconscious. In this regard, the drop in blood pressure results in significantly less blood filling the ventricles, such that there is simply not enough incoming blood to pump. Hence, overall blood pressure is not significantly increased merely by pumping the heart faster, and the aforementioned cerebral hypoperfusion still occurs resulting in unconsciousness. Indeed, depending upon the programming of the pacemaker, it may take five to eight seconds or more before the pacemaker begins increasing the heart rate.

Accordingly, it would be highly desirable to provide an improved cardiac pacing device capable of promptly pacing the heart upon detection of a sudden drop in heart rate caused by vasovagal syncope or other conditions, so as to prevent a sudden drop in blood pressure to thereby more effectively prevent loss of consciousness.

SUMMARY OF THE INVENTION

In accordance with the invention, a method is provided for use in an implantable cardiac pacing device for preventing a sudden heart rate drop. With the method, an intrinsic heart rate is sensed and the heart is selectively paced while applying rate smoothing to the intrinsic ventricular rate, regardless of the intrinsic ventricular heart rate. The rate smoothing technique may also be applied to the atrial rate as well.

In an exemplary embodiment, wherein the implantable cardiac pacing device is a pacemaker or ICD, rate smoothing is applied so as to prevent a sharp heart rate increase while still permitting a sharp heart rate increase as may be required, for example, as a result of sudden exertion. This rate smoothing technique is referred to herein as a "downward" rate smoothing technique. By employing downward rate smoothing to prevent a sudden drop in heart rate, pacing can begin promptly upon detection of the drop in heart rate. This is in contrast with the conventional vasovagal syncope detection techniques discussed above wherein no pacing may occur until well after the heart rate has dropped and hence well after the blood pressure of the patient has dropped, possibly resulting in loss of consciousness. Also, by applying downward rate smoothing regardless of intrinsic ventricular heart rate, the rate smoothing prevents a sharp drop in heart rate from an otherwise normal heart rate as typically occurs during vasovagal syncope. In addition to helping to prevent vasovagal syncope, the rate smoothing technique also helps prevent long sinus pauses, which sometimes result in a malignant arrhythmia.

In a specific exemplary embodiment, the downward rate smoothing is applied during the determination of an escape interval as follows. After each newly paced or sensed heart beat, the device determines a sensor indicated rate ("SIR"), a base rate interval, and a measured rate interval ("MRI"). Then the measured rate interval is compared with a filtered rate interval ("FRI") initially set to a default value. If the MRI is less than the previous FRI, then the FRI is reset to be equal to the greater of the MRI and the previous FRI, minus a decrement value. If the MRI is not less than previous FRI, then the FRI is reset to be equal to the lesser of the MRI and the previous FRI, plus an increment value. In either case, once the FRI has been reset, the escape interval is then set to the lesser of the SRI, the base rate interval and the FRI, plus a predetermined time interval. During each cycle, if a sensed beat is not detected before the escape interval elapses, a pacing pulse is applied to the heart.

This downward rate smoothing algorithm has the effect of slowing a sudden decrease in heart rate, but not impeding a sharp increase in heart rate, as may occur as a result of orthostatic stress. Hence, if the heart rate needs to increase properly as a result of sudden vigorous activity, the ventricular rate smoothing algorithm does not prevent that increase.

Apparatus embodiments of the invention are also provided. Other features, advantages and aspects of the invention are either described below or will be apparent from the descriptions below in combination with the accompanying drawings.

BRIEF DESCRIPTION OF THE DRAWINGS

Further features and advantages of the invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
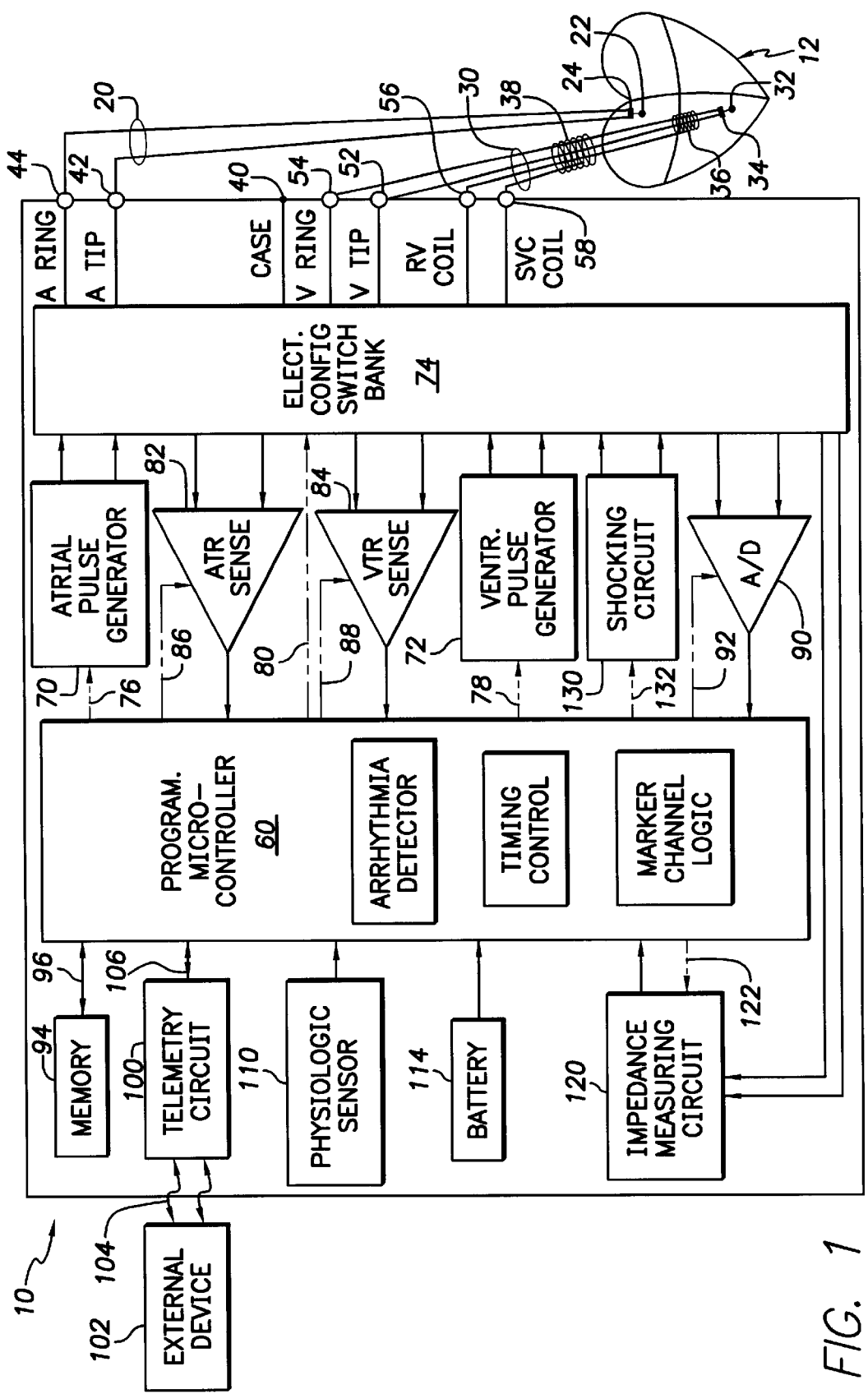
FIG. 1 is a functional block diagram of a dual-chamber implantable stimulation device illustrating the basic elements of a stimulation device which can provide cardioversion, defibrillation and pacing stimulation and which is programmed to perform ventricular rate smoothing in accordance with an exemplary embodiment of the invention.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/196,898, "A Self-Anchoring Coronary Sinus Lead" (Pianca et. al), and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses, that is well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the present device utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 28 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the stimulation device 10, which employs shocking therapy, the battery must be capable of operating at low current drains for long periods of time, and then be capable of providing high-current pulses (for capacitor charging) when the patient requires a shock pulse. The battery 114 must also have a predictable discharge characteristic so that elective replacement time can be detected. Accordingly, the device employs lithium/silver vanadium oxide batteries, as is true for most (if not all) such devices to date.

As further shown in FIG. 1, the device preferably includes an impedance measuring circuit 120 which is enabled by the microcontroller 60 by a control signal 122. The impedance measuring circuit 120 is not critical to the present invention and is shown for only completeness.

It is the primary function of the present invention to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
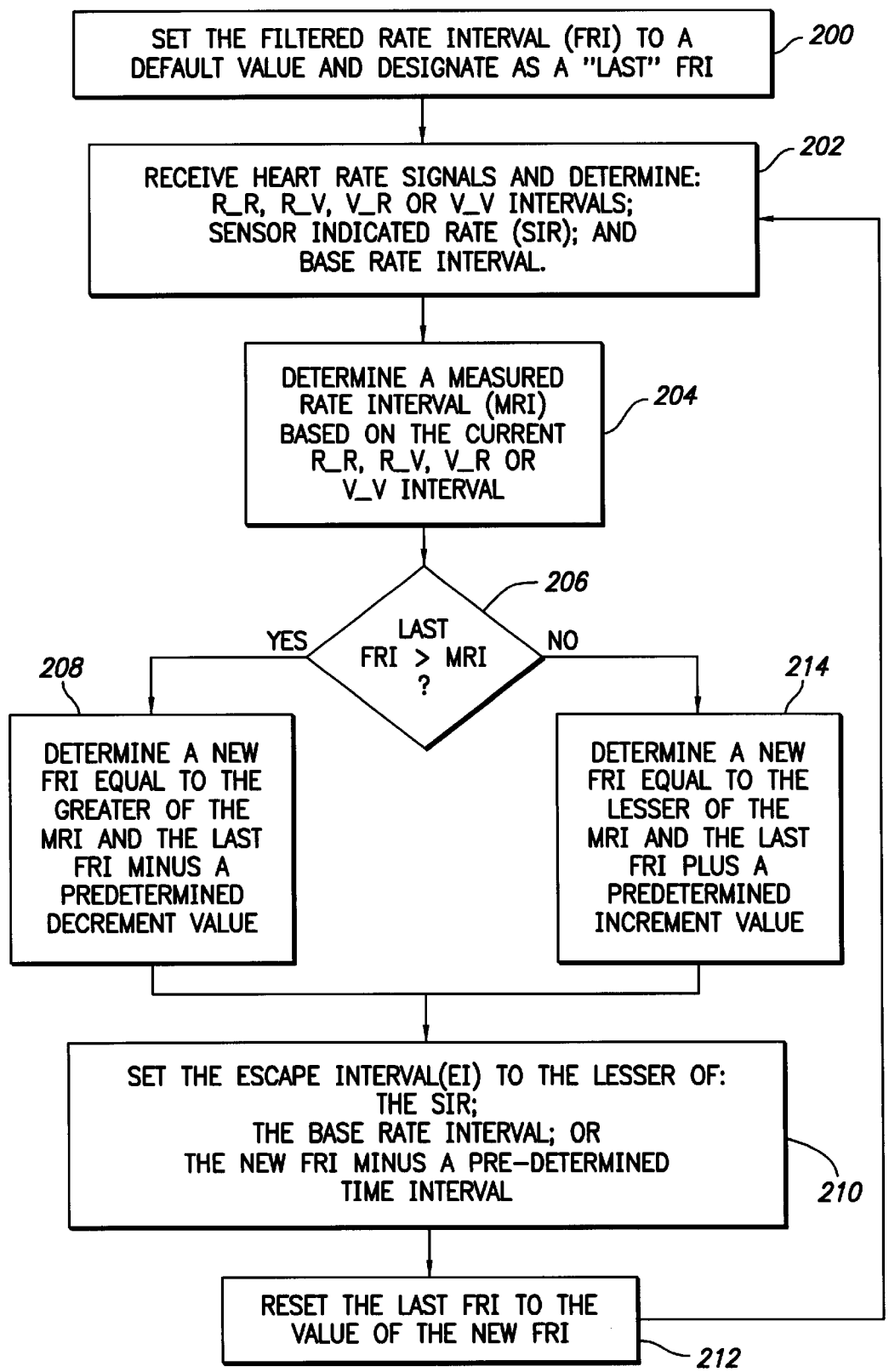
FIG. 2 is a flow chart illustrating steps performed by a controller of the device of FIG. 1 for performing ventricular rate smoothing.

FIG. 2 illustrates, at a high level, the operation of controller 60 as it pertains to a calculation of an escape interval for use in pacing the heart wherein the escape interval is calculated by applying a ventricular rate smoothing algorithm to the ventricular heart rate. In the flow chart, various steps performed by the controller are summarized in individual "blocks" where a microcontroller (or equivalent) is employed, the flow chart of FIG. 2 provides the basis for "control" program that may be used by such a microcontroller (or equivalent) to effectuate the desired control of the stimulation device. Those skilled in the art may readily write such a control program based on the flow charts and other descriptions presented herein.

Now considering FIG. 2 in greater detail, the figure illustrates a technique for calculating an escape interval which may be employed by controller 60 of FIG. 1 while the pacemaker or ICD is set to VDD/R or VVI/R modes of operation. The escape interval represents a period of time subsequent to each paced or sensed beat wherein, if another sensed beat is not detected, the controller triggers a paced beat. Hence, so long as the intrinsic heart rate is faster than an escape interval rate, no pacing occurs. As will be further described, the escape interval is determined, in part, by an FRI which is iteratively adjusted subsequent to each paced or sensed beat. To adjust the FRI, the rate smoothing algorithm takes into account a programmed based rate interval, a measured rate interval ("MRI"), and a calculated sensor indicated rate ("SIR"). The MRI is set equal to one of the following measured intervals: R_R, R_V, V_R and V_V. R represents a sensed ventricular beat. V represents a paced ventricular pulse. R_R thereby represents the time interval between two consecutive sensed ventricular beats; V_V represents the time interval between a pair of consecutive paced ventricular beats and so on. If the pacemaker or ICD is programmed to AAI mode, wherein pacing and sensing is performed only in the atria, with detection of a sensed event inhibiting administration of a pacing pulse, then the controller instead uses the following atrial intervals. P_P, P_A, A_P, A_A, wherein P represents a sensed atrial beat, and A represents a paced atrial beat. The SIR may be calculated using conventional techniques. Further information regarding SIR is provided in U.S. Pat. No. 5,292,341 to Snell, issued Mar. 8, 1994 and entitled "Method And System For Determining And Automatically Adjusting The Sensor Parameters Of A Rate-Responsive Pacemaker", which is incorporated by reference herein. When operating in the DDD or DDD/R mode of operation, the atrial escape interval may be used to establish the escape interval as is commonly known in the art.

Initially, at step 200, controller 60 sets the FRI to a default value and designates the default value as a "last" FRI. Preferably, the default value is pre-programmed based upon an average expected FRI, for example, 1,000 milliseconds "msec". Thereafter, beginning at step 202, the pacemaker receives heart rate signals from which the controller determines the SIR and the current ventricular interval (either R_R, R_V, V_R or V_V). At step 204, the controller sets the MRI to be equal to the current ventricular interval. At step 206, the controller then determines whether the MRI is less than the last FRI. If so, then at step 208 the controller determines a new FRI by subtracting a predetermined rate decrement value from the last FRI then setting the new FRI equal to the greater of the MRI and the last FRI as adjusted by the decrement value. Thereafter, at step 210, the controller determines the escape interval based on the SIR, the based rate interval, and the new FRI. More specifically, the controller determines which value is lowest: the SIR, the base rate interval, or the new adjusted FRI minus a predetermined time interval, then sets the escape interval to be equal to the lowest of those values. In other words, the escape interval is set to the new adjusted FRI so long as the new adjusted FRI is less than both the SIR and the base rate interval. Then, at step 212, the controller resets the last FRI equal to the new FRI value and returns to step 202 for further processing. If, at step 206, the MRI is found to be greater than or equal to the last FRI, then the controller performs step 214 to determine the new FRI by setting the new FRI equal to the lesser of the MRI and the last FRI, plus a predetermined increment value. Hence, subsequent to step 206, the FRI is either adjusted upwardly or downwardly depending upon the current value of the MRI and the previous value of the FRI.

Steps 202–212 are performed iteratively for each new paced or sensed ventricular beat to iteratively adjust the escape interval so as to prevent a sharp drop in the ventricular rate while permitting a sharp increase in ventricular rate. This assumes that the pacemaker or ICD is set to either VDD/R or VVI/R modes of operation. If set to DDX/R or AAIR, the escape interval is the atrial pacing interval. Thus, the algorithm may be employed for both atrial or ventricular rate smoothing, depending upon the mode of operation of the device. Insofar as atrial rate smoothing is concerned, a related atrial rate smoothing technique is described in U.S. Pat. No. 5,549,649 to Florio et al., dated Aug. 27, 1996, entitled "Programmable Pacemaker Including an Atrial Rate Filter for Deriving a Filtered Atrial Rate Used for Switching Pacing Modes", which is incorporated herein by reference. Atrial rate smoothing is provided within the Florio patent only while the pacemaker ICD is set to an AMS mode, whereby the pacemaker or ICD automatically switches its mode of operation from an atrial tracking mode to a non-atrial tracking mode in the event that the atrial rate exceeds a predetermined upper rate limit. As explained in the Florio et al. patent, certain patients may exhibit atrial rates that vary significantly over short periods of time. In such patients, as a result of the fluctuations, frequent mode switching may occur. Accordingly, atrial rate smoothing is applied while AMS is enabled to reduce the degree of fluctuations in the atrial rate to thereby reduce the risk of too frequent mode switching. In other words, by applying rate smoothing to the atrial rate, the atrial rate will vary more slowly with time, thereby crossing the rate threshold less frequently thereby triggering mode switch operations less frequently. With the present invention, by applying rate smoothing to both the atrial and ventricular channels, sudden rate drops are prevented regardless of whether AMS is enabled. With AMS enabled, however, the rate smoothing on the atrial channel also helps prevent the aforementioned frequent mode switches.

The algorithm illustrated in FIG. 2 may also be represented using the following pseudo-code:

```
If (Filtered_Rate_Interval(n-1)>=Measured_Rate_Interval(n))
    Filtered_Rate_Interval(n)=maximum Measured_Rate_Interval(n),
        Filtered_Rate_Interval(n-1)-Delta_Dec)
Else
    Filtered_Rate_Interval(n)=maximum (Measured_Rate_Interval(n),
        Filtered_Rate_Interval(n-1)+Delta_Inc)
Escape Interval=minimum (Filtered_Rate_Interval(n)+Delta_EI,
    Sensor_indicated_Rate_Interval(n)*, Base_Rate_Interval)
```

Note that, if the sensor of the device is deactivated, the SIR interval is not used in the aforementioned technique. Also, if the device is operating within an AMS mode, then, instead of using the base rate interval, a separate mode switch alternate rate interval may instead be employed. Also, depending upon the implementation, the various delta values (delta_dec, delta_inc, delta_EI) can be varied or programmed as needed by the physician. In other cases, the device may be preprogrammed with set values. Exemplary values are as follows. The delta_EI value, also referred to as the time interval of step 210, may be 10 msec, 20 msec, 30 msec, 40 msec or 50 msec. The delta_dec value, also referred to as the predetermined decrement value of step 208, may be set to a value in the range of 10–100 msec, preferably 39 msec. The delta_inc value, also referred to as the predetermined increment value of step 214, may be set in the range of 5–30 msec, preferably 23 msec. Depending upon the implementation though, different values may be employed, and these values may be optimized based upon routine experimentation.

Figure 3:
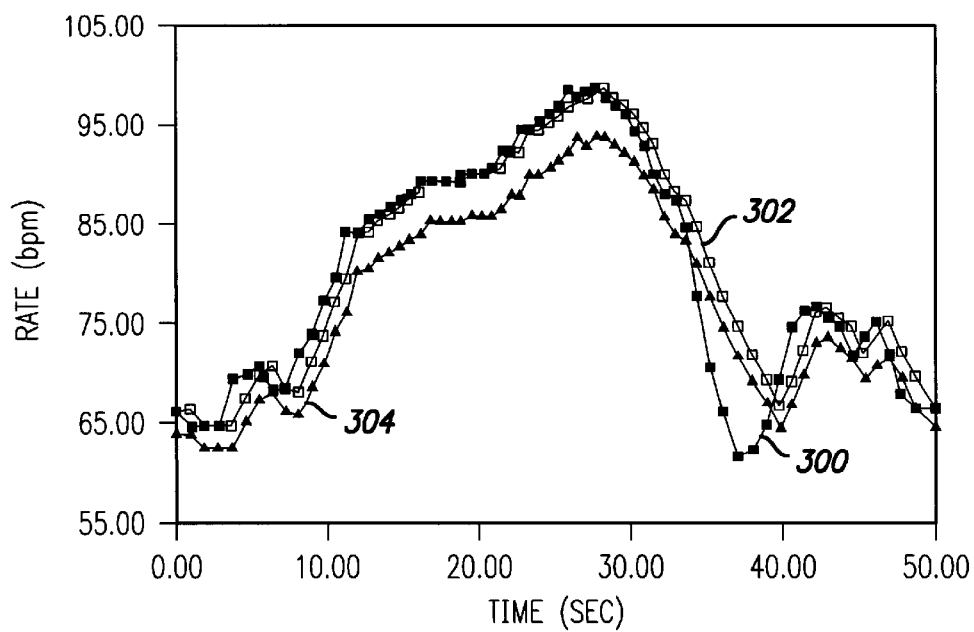
FIG. 3 is a graph illustrating a simulation of sensed rate, filtered rate, and escape rate based on a period of normal sinus rhythm. Note that if pacing were provided using the escape rate as is the intended operation of the algorithm, there would be no sensed events below the escape rate because the escape rate would be greater than the sensed rate.
Figure 4:
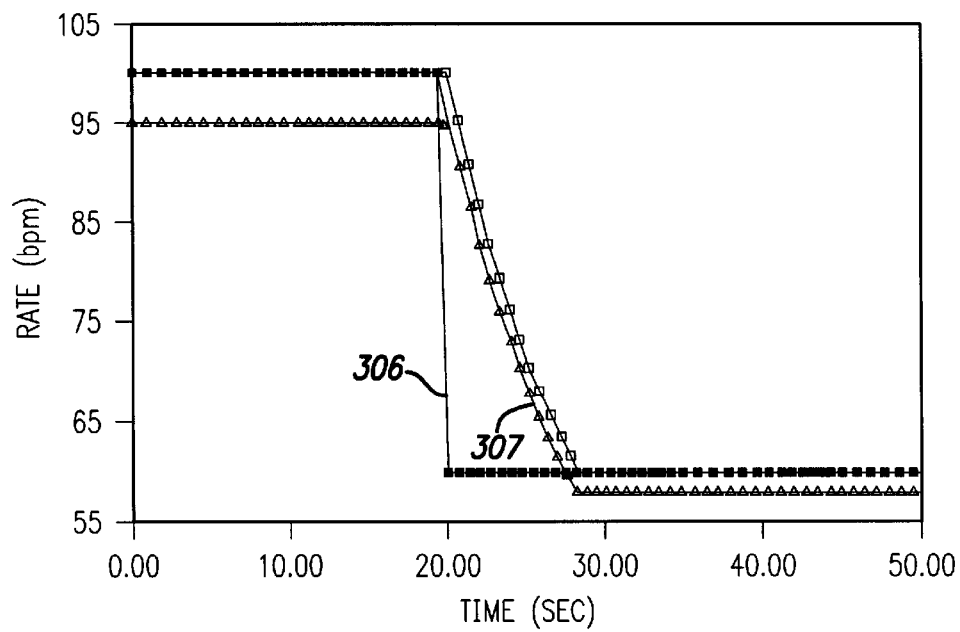
FIG. 4 is a graph illustrating sensed rate, filtered rate, and escape rate for an episode of vasovagal syncope.

Thus, the rate smoothing algorithm of FIG. 2 operates to pace the heart during a sudden intrinsic ventricular heart rate drop so as to permit the heart rate to slowly decrease to the intrinsic rate. The algorithm also tracks a sudden increase in ventricular rate, but does not pace during the increase, so as to permit any patient to benefit from a sharp increase in heart rate as may be required upon engaging in sudden vigorous activities. These features are illustrated within the remaining figures. Briefly, FIG. 3 illustrates the sensed rate 300, the filtered rate 302, and the escape rate 304 while the patient is within a normal sinus rhythm. In the example of FIG. 3, the intrinsic rate of the patient increases slowly, but substantially, over a period of 30 seconds from 65 beats per minute (bpm) to about 100 bpm. This may be caused, for example, by a gradual increase in physical exertion. Thereafter, the intrinsic rate decreases gradually as is consistent with the termination of the physical exertion. Whenever the escape rate is lower than the sensor rate, no pacing occurs. Pacing only occurs if the escape rate exceeds the sensed rate. In the example of FIG. 3, no pacing occurs as the heart rate increases. However, when the heart rate begins to decrease, the escape rate decreases more slowly than the sensed rate, permitting pacing. FIG. 4 illustrates a case of vasovagal syncope wherein the sensed rate 306 of the patient drops suddenly and significantly from about 100 bpm to about 60 bpm. In this case the base rate is equal to 60 ppm. If the heart rate were permitted to drop that significantly, the patient would likely lose consciousness immediately as a result of the associated drop in blood pressure. However, by applying the rate smoothing technique of the invention, the heart rate is paced at the escape rate 307 so as to decrease more slowly and smoothly. Indeed, the paced rate does not decrease all the way down to 60 bpm for nearly 10 seconds. In other words, the heart is paced throughout the period of time from the sudden drop in sensed rate until the escape rate drops below the sensed rate. The gradual decrease in heart rate is likely to be sufficient to prevent sudden loss of consciousness by the patient. Even if a loss of consciousness ultimately occurs, the loss of consciousness is probably delayed by five to ten seconds, thereby giving the patient time to take remedial action, such as, if driving, to pull the vehicle over to the side of the road or to avoid any other potentially dangerous situation.

Figure 5:
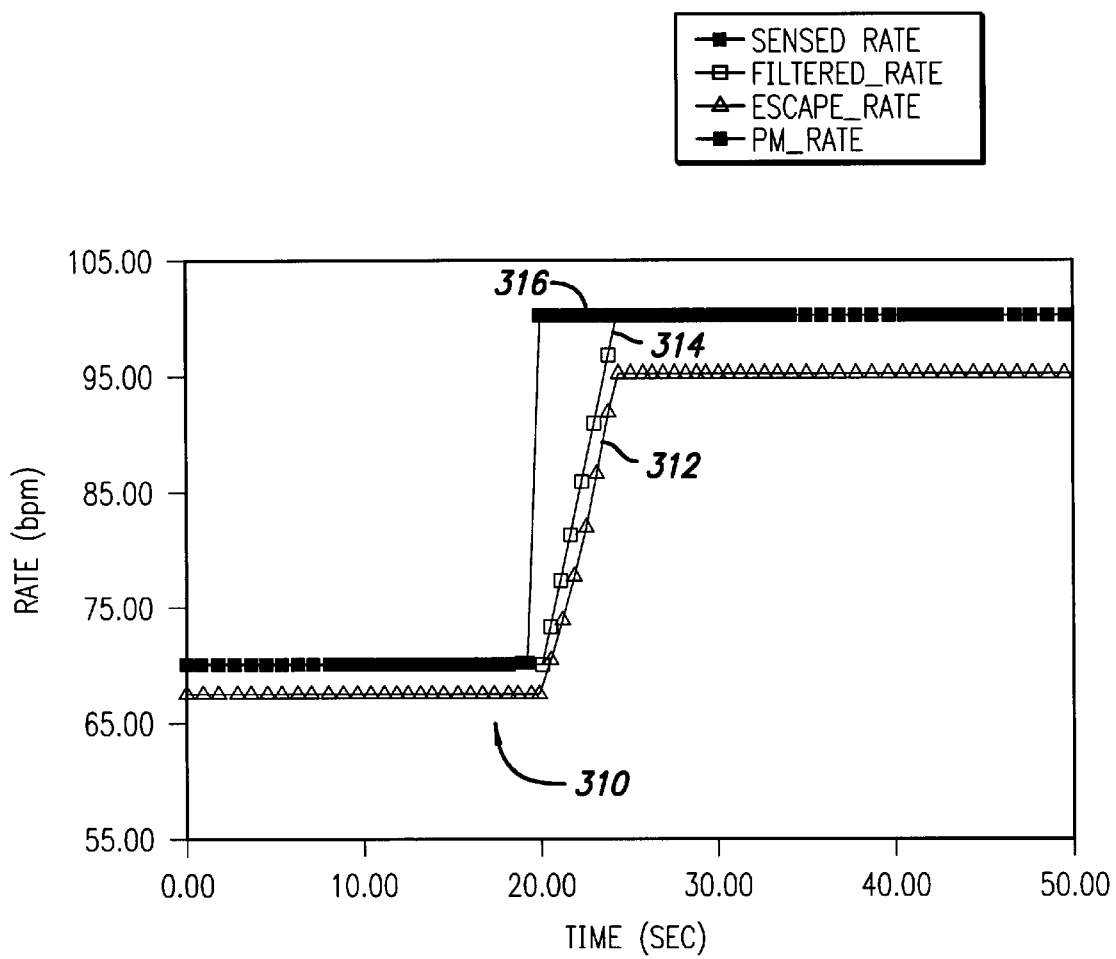
FIG. 5 is a graph illustrating sensed rate, filtered rate, and escape rate for a sample of sinus rhythm involving a very sharp increase in heart rate such as may occur with sudden orthostatic stress.

FIG. 5 illustrates a case wherein a sudden increase in ventricular rate occurs beginning at time 310. The escape rate 312 increases gradually over the next five seconds until the filtered rate 314 reaches the elevated sensed rate 316 of 100 bpm. Since the escape rate remains below the sensed rate at all times, no pacing occurs. Thus, the rate smoothing algorithm does not interfere with the sharp increase in heart rate. Of course, if the controller determines that the sharp increase in heart rate may have been due to tachyarrhythmia, appropriate therapy may be applied to the heart to terminate the arrhythmia.

What has been described is a rate smoothing technique which may be applied to both ventricular and atrial heart rates so as to prevent sudden drop in heart rate without interfering with a sharp increase in heart rate. Preferably, the pacemaker or ICD is configured so that a physician may activate or deactivate the rate smoothing algorithm based upon the needs of the particular patient. Hence, if the patient is prone to vasovagal syncope or other conditions that may result in a sharp rate in heart rate, the rate smoothing algorithm is preferably activated. For patients not subject to sharp drops in heart rate, the rate smoothing algorithm may either be deactivated or employed only in connection with smoothing the atrial rate while within an atrial tracking mode with AMS activated.

The specific examples herein are intended merely to illustrate the invention and should not be construed as limiting the scope of the invention. Rather, principles of the invention are applicable to other systems and for use to achieve other ends, such as for use with other types of syncope.

What is claimed is:

1. In an implantable cardiac pacing device, a method for preventing a sudden rate drop in the heart rate of a patient comprising:

sensing an intrinsic heart rate of the patient; and selectively pacing the heart while applying rate smoothing to the heart rate, with the rate smoothing being applied regardless of the magnitude of the ventricular heart rate;

wherein the step of selectively pacing the heart is performed while applying downward rate smoothing so as to prevent a sharp heart rate decrease which is hemodynamically compromising and to permit a sharp heart rate increase;

wherein the step of selectively pacing the heart comprises the steps of:

generating an escape rate based in part on the intrinsic heart rate with the escape rate set to be greater than the intrinsic rate during any sharp drop in the intrinsic rate which is hemodynamically compromising and less than the intrinsic rate during any sharp rate increase; and applying pacing pulses to the heart only while the escape rate is greater than the intrinsic rate; and wherein the step of generating an escape rate includes the steps of:

determining a filtered rate interval (FRI), a measured rate interval (MRI), and a sensor indicated rate (SIR);

if the FRI is greater than the MRI, resetting the FRI to a maximum of the MRI and the FRI minus a predetermined FRI decrement; and if the FRI is not greater than the MRI, resetting the FRI to a minimum of the MRI and the FRI plus a predetermined FRI increment; and setting an escape interval equal (EI) to a lesser of the reset FRI plus a predetermined EI increment, the SIR, and a predetermined base rate interval.

2. In an implantable cardiac pacing device, a system for preventing a sudden rate drop in the heart rate of a patient comprising:

means for sensing an intrinsic ventricular heart rate of the patient;

means for detecting a physiological state of the patient;

means for determining an escape rate based in part on the intrinsic rate with the escape rate set to be greater than the intrinsic rate during any sharp hemodynamically compromising drop in the intrinsic rate and less than the intrinsic rate during any sharp rate increase, the means for determining an escape interval further comprises:

determining a filtered rate interval (FRI), a measured rate interval (MRI), and a sensor indicated rate (SIR), the SIR determined by the means for detecting a physiological state of the patient;

if the FRI is greater than the MRI, resetting the FRI to a maximum of the MRI and the FRI minus a predetermined FRI decrement; and if the FRI is not greater than the MRI, resetting the FRI to a minimum of the MRI and the FRI plus a predetermined FRI increment; and setting the EI to a lesser of the reset FRI plus a predetermined EI increment, the SIR, and a predetermined base rate interval; and means for generating stimulation pulses for applying to the heart, with the stimulation pulses being generated only while the escape rate is greater than the intrinsic rate.

3. In an implantable cardiac pacing device, a system for preventing a sudden rate drop in the heart rate of a patient comprising:

a sensor for sensing an intrinsic heart rate of the patient;

a physiologic sensor to detect exercise state of the patient;

a pulse generator for generating stimulation pulses for applying to the heart; and a controller for selectively controlling the pulse generator to generate stimulation pulses while applying rate smoothing to a ventricular rate, with the rate smoothing being applied regardless of the magnitude of the heart rate;

wherein the controller applies downward rate smoothing so as to prevent a sharp drop in heart rate which is hemodynamically compromising and to permit a sharp increase in heart rate;

wherein the controller generates an escape rate based in part on the intrinsic rate with the escape rate set to be greater than the intrinsic rate during any sharp drop in the intrinsic heart rate which is hemodynamically compromising and less than the intrinsic rate during any sharp rate increase and controls the pulse generator to apply stimulation pulses to the heart only while the escape rate is greater than the intrinsic rate; and wherein the controller determines an escape interval (EI) by:

determining a filtered rate interval (FRI), a measured rate interval (MRI), and a sensor indicated rate (SIR), the controller determining the SIR from the physiologic sensor;

if the FRI is greater than the MRI, resetting the FRI to a maximum of the MRI and the FRI minus a predetermined FRI decrement; and if the FRI is not greater than the MRI, resetting the FRI to a minimum of the MRI and the FRI plus a predetermined FRI increment; and setting the EI to a lesser of the reset plus a predetermined EI increment, the SIR, and a predetermined base rate interval.

4. In an implantable cardiac pacing device, a method for preventing a sudden hemodynamically compromising rate drop in the heart rate of a patient comprising:

sensing an intrinsic heart rate of the patient; and selectively pacing the heart by generating an escape rate to apply rate smoothing to the heart rate;

wherein the generating an escape rate comprises:

determining a filtered rate interval (FRI), a measured rate interval (MRI), and a sensor indicated rate (SIR);

if the FRI is greater than the MRI, resetting the FRI to a maximum of the MRI and the FRI minus a predetermined FRI decrement; and if the FRI is not greater than the MRI, resetting the FRI to a minimum of the MRI and the FRI plus a predetermined FRI increment; and setting an escape interval equal (EI) to a lesser of the reset FRI plus a predetermined EI increment, the SIR, and a predetermined base rate interval.

5. The method of claim 4 wherein the selectively pacing the heart is performed while applying a downward rate smoothing so as to prevent a sham hemodynamically compromising heart rate decrease while permitting a sharp heart rate increase.

6. The method of claim 5 wherein the selectively pacing the heart further comprises:

generating the escape rate based in part on the intrinsic heart rate with the escape rate set to be greater than the intrinsic rate during a sharp hemodynamically compromising drop in the intrinsic rate and less than the intrinsic rate during a sharp rate decrease; and applying pacing pulses to the heart when the escape rate is greater than the intrinsic rate.

7. The method of claim 4 further comprising applying pacing pulses to the heart only while the escape rate is greater than the intrinsic rate.

8. In an implantable cardiac pacing device, a system to prevent a sudden hemodynamically compromising rate drop in the heart rate of a patient comprising:

a sensor to sense an intrinsic heart rate of the patient;

a physiologic sensor to detect exercise state of the patient;

a pulse generator to provide stimulation pulses to the heart; and a controller to control the pulse generator to apply simulation pulses to the heart;

wherein the controller generates an escape rate based in part on an intrinsic rate with the escape rate set to be greater than the intrinsic rate during a sharp hemodynamically compromising drop in the intrinsic heart rate and less than the intrinsic rate during any sharp rate increase, and wherein the controller determines an escape interval (EI) by:

determining a filtered rate interval (FRI), a measured rate interval (MRI), and a sensor indicated rate (SIR), the controller determining the SIR from the physiologic sensor;

if the FRI is greater than the MRI, resetting the FRI to a maximum of the MRI and the FRI minus a predetermined FRI decrement; and if the FRI is not greater than the MRI, resetting the FRI to a minimum of the MRI and the FRI plus a predetermined FRI increment; and setting the EI to a lesser of the reset FRI plus a predetermined EI increment, the SIR, and a predetermined base rate interval.

9. The system of claim 8 wherein the controller applies downward rate smoothing to prevent a sharp hemodynamically compromising drop in the heart rate while permitting a sharp increase in the heart rate.

* * * * *